US006686842B1

(12) United States Patent
Afilani

(10) Patent No.: US 6,686,842 B1
(45) Date of Patent: *Feb. 3, 2004

(54) ANIMATE ENTITY'S LINE-OF-BEARING LOCATION DEVICE AND METHOD LINKING SPECIES-SPECIFIC NON-UNIFORM-ELECTRIC FIELD PATTERN OF HEART'S ECG TO DIELECTROPHORESIS

(75) Inventor: Thomas Afilani, Jersey Shore, PA (US)

(73) Assignee: DKL International, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/071,806

(22) Filed: May 4, 1998

Related U.S. Application Data

(63) Continuation-in-part of application No. 08/758,248, filed on Nov. 27, 1996, now Pat. No. 5,748,088.

(51) Int. Cl.[7] .............................................. G08B 23/00
(52) U.S. Cl. .................... 340/573.1; 340/561; 340/562; 340/568.1; 324/71.1; 324/72; 324/452; 324/457
(58) Field of Search ............................. 340/573.1, 561, 340/562, 563, 564, 565, 566, 567, 568.1; 324/71.1, 72, 452, 457

(56) References Cited

U.S. PATENT DOCUMENTS

| 3,771,152 A | 11/1973 | Dettling et al. |
| 3,836,899 A | 9/1974 | Duvall et al. |
| 3,898,472 A | 8/1975 | Long |

(List continued on next page.)

FOREIGN PATENT DOCUMENTS

JP      1-113692      5/1989

WO      WO 98/24077      6/1998

OTHER PUBLICATIONS

Keiichi, M. "Detecting Circut Of Signal," Patent Abstracts of Japan, vol. 007, No. 278, (p. 242), Dec. 1983 & JP 58 154671 A (Sep. 1983).

Murray, Dale W., "Physical Examination of the DKL Life-Guard™ Model 3," Oct. 30, 1998, (pp. 1–53).

Murray, Dale W. et al., "Double–Blind Evaluation of the DKL LifeGuard Model 2," Apr. 29, 1998, (21 pages).

Moore, A.D., "Electrostatics and its Applications," Electrical and Computer Engineering Dept., University of Michigan, Ann Arbor, (4 pages).

Pohl, Herbert A., "Dielectrophoresis: The Behavior of Neutral Matter in Nonuniform Electric Fields," (7 pages).

(List continued on next page.)

*Primary Examiner*—Nina Tong
(74) *Attorney, Agent, or Firm*—Nixon & Vanderhye P.C.

(57) ABSTRACT

The dielectrophoretic force caused by the non-uniform electric field squared spatial gradient three-dimensional pattern uniquely exhibited by a predetermined type of entity can be detected by a locator device. A human operator holds the device in hand to thereby electrically and dielectrically connect the device to the human operator. The human operator's naturally occurring very low electrical decay time constant is increased through electronic circuitry externally connected to the device. The device is held in a balanced nearly horizontal state, and the operator scans the device in a constant speed uniform linear motion back and forth. An antenna extends from the front of the device, and both are acted on by the dielectrophoretic force. This force results in a subsequent resulting torque, acceleration, vibration or any other measurable quantifiable manifestation of the force about the handle's pivot line hence driving the device and its antenna toward the direction and position of any entities of the predetermined type that are within range.

16 Claims, 14 Drawing Sheets

U.S. PATENT DOCUMENTS

| | | | |
|---|---|---|---|
| 4,138,641 A | | 2/1979 | Karlin et al. |
| 4,316,180 A | | 2/1982 | LeVert |
| 4,320,766 A | | 3/1982 | Alihanka et al. |
| 4,339,709 A | | 7/1982 | Brihier |
| 4,476,004 A | * | 10/1984 | Pohl .................. 435/285.2 |
| 4,621,258 A | | 11/1986 | Campman |
| 4,632,762 A | | 12/1986 | Ramsland |
| 4,956,065 A | * | 9/1990 | Kaler et al. ............ 204/547 |
| 5,019,804 A | | 5/1991 | Fraden |
| 5,300,889 A | * | 4/1994 | Bakhoum .............. 324/457 |
| 5,419,337 A | * | 5/1995 | Dempsey et al. ....... 600/515 |
| 5,436,613 A | | 7/1995 | Ghosh et al. |
| 5,446,591 A | | 8/1995 | Medlock |
| 5,748,088 A | * | 5/1998 | Afilani ................ 340/573.1 |
| 6,264,815 B1 | * | 7/2001 | Pethig et al. ............ 204/547 |

OTHER PUBLICATIONS

The New Lexicon "Webster's Encyclopedic Dictionary" of the English Language, (definitions of "electrokinetics," "electrophoresis," "kinesis," and "kinetics"; (5 pages).

Voss, D., "New Physics' Finds a Haven at the Patent Office," Science, vol. 284, May 21, 1999 (pp. 1252–1254).

* cited by examiner

ANIMATE ENTITY'S LINE-OF-BEARING LOCATION DEVICE AND METHOD LINKING SPECIES-SPECIFIC NON-UNIFORM-ELECTRIC FIELD PATTERN OF HEART'S ECG TO DIELECTROPHORESIS

This application is a continuation in part of U.S. patent application Ser. No. 08/758,248, filed Nov. 27, 1996 now U.S. Pat. No. 5,748,088.

BACKGROUND OF THE INVENTION

The present invention relates to methods and apparatus for locating various entities, including human beings and animals, by observing and detecting a force and subsequent resulting torque, acceleration, vibration or other measurable, quantifiable manifestation of the force created by the non-uniform three-dimensional electric field spatial gradient pattern exhibited uniquely by an entity and being detected by the device of the present invention as used by the device's human operator.

The detection of visually obscured entities has many uses in fire-fighting, search and rescue operations, law enforcement operations, military operations, etc. While prior art devices are known that detect humans, animals and other materials, some by measuring changes in an electrostatic field, none of the operable prior art devices uses the force resulting from the non-uniform electric field squared spatial gradient three-dimensional pattern exhibited uniquely by an entity to indicate the precise location and line-of-bearing direction of the subject entity relative to the device's human operator.

By using an electrokinetic effect, dielectrophoresis, which induces a force and subsequent resulting torque on an antenna and other component parts of the device, the present invention gives a rapid line-of-bearing directional location indication of the subject entity. A meter can also be provided to indicate the direction of strongest non-uniform electric field squared spatial gradient signal strength for those situations where the dielectrophoretic force and subsequent resulting torque, acceleration, vibration or any other measurable quantifiable manifestation of the force is extremely small and difficult to detect.

It should be noted that while the present invention works for many different types of entities, a primary use of the present invention is to locate animate entities and, in particular, human beings, irrespective of the presence or absence of obscuring material structures (walls, trees, earthen mounds, etc.), of rfi and emi interference signals, of adverse weather conditions, and of day or night visibility conditions.

The nature and source of an animate entity's (in particular human) electric field and its spatial gradient being detected in the dielectrophoresis effect generating the directionally self-correcting force and subsequent torque characteristic of an animate entity, line-of-bearing locator device has been discussed in *Bioelectromagnetism*, R. Plonsey et al. (eds.), Oxford University Press (1995) and R. A. Rhoades, *Human Physiology*, Harcourt Brace Javanioch (1992). The empirical evidence in the case of humans is quite persuasive that human heart electro-physiology generates by far the strongest electric field and spatial gradient pattern. In human physiology, the central and peripheral nervous system neurons, the sensory system cells, the skeletal muscular system, the independent cardiac conduction cells, and the cardiac muscle system cells operate via polarization and depolarization phenomena occurring across all respective cellular membranes. The electric potentials associated with these polarization fluctuations are routinely used at a human body surface for empirical correlation/clinical diagnostic purposes, such as the ECG for the heart and the EEG for the brain. The heart has by far (about a factor of 70 compared to the brain) the largest voltage, electric field and electric field spatial gradient pattern in the human body compared to the other operating systems mentioned above.

The human heart is a special case wherein the conduction SA node, the VA node, Purkinje fibers, etc. provide high polarization (95 mV) and very rapid (ms) depolarization (110 mV) potentials. The dipole electric field fluctuations are periodic and frequent. The carrier frequency of de- and re-polarizations occurs in a range of 72 for adults to 120 in babies (beats per min. or 1.2 to 2.0 Hz). The frequency spectra of ECG patterns have main lobes at about 17 Hz. In sub-ULF (0 to 3 Hz) and ULF (3 to 30 Hz) frequency ranges, the electric and magnetic fields are quasi-static and are not strongly coupled as "EM waves," and EM activities detected in these ranges have a predominantly magnetic or electric nature (heart electric field is many times larger than heart magnetic field, see *Bioelectromagnetism*, R. Plonsey et al., Oxford University Press (1995)) as discussed in D. O. Carpenter, *Biological Effects of EM Fields*, Academic Press (1994). Normal neuron or cardiac activity aberrations, such as strokes/heart attacks, create a temporary or permanent depolarization resulting in loss of polarization and an inability to repolarize. The heart's resultant polarization electric field distribution pattern has a high degree of spatial non-uniformity and can be characterized as a moving dipolar charge distribution pattern during each heartbeat. The human heart electric field pattern is unique and is thus able to be detected.

Traditionally, inanimate dielectrics have been found to exhibit three main and one rare polarization modes (electronic, atomic, orientation and the rare nomadic) as discussed in *Properties of Polymers*, D. W. van Krevelen, Elsevier Publ. (1976); A. R. von Hippel, *Dielectrics and Waves*, John Wiley and Sons (1954); *Dielectric Materials & Applications*, A. R. von Hippel (ed) John Wiley (1954); H. A. Pohl, *Dielectrophoresis*, Cambridge University Press (1978). These modes lead addivtively in the sequence given as one goes from UHF ($10^{18}$ Hz) to ULF (3 to 30 Hz) to sub-ULF (0 to 3 Hz) dielectric constraints of 1.0 for air to 78 for water with essentially all plastics in a 3 (PVC) to 14 (Bakelite) range. There are rare outriders like the solvent NMMA at 191, Se at $1\times10^3$ and ferroelectric $BaTiO_3$ and rare nomadic polymers $(CS_2)_x$ at $2\times10^4$ and PAQR carbazole at $3 \times 10^5$.

Mammalian physiology results for the ULF dielectric constants of mammalian (human) living tissues, wherein mammalian (human) tissues are 70% volume water (dielectric constant 78), show that all the ordinary animate human tissues, like heart, brain, liver, heart, blood, skin, lung and even bone, have quite extraordinarily high ULF dielectric constants ($10^5$ to $10^7$), found only very rarely in usual inanimate dielectric materials. See *Biomedical Engineering Handbook*, J. D. Bronzino (ed.), CRC Press (1995); *Physical Properties of Tissue*, F. A. Duck, Academic Press (1990); H. P. Schwan, *Advances in Biological and Medical Physics*, 5, 148 to 206 (1957); E. Grant, *Dielectric Behaviour of Biological Molecules*, Oxford Univ. (1978) and *Handbook of Biological Effects of Electromagnetic Fields*, 2nd Ed., C. Polk et al., CRC Press (1996). It is also found that as the animate tissues die these extraordinarily high ULF dielectric constants collapse downward greatly to more normal inanimate values over time as the dying tissue becomes, over time, inanimate. The reason for the great differences is the routine occurrence of other polarization modes in animate materials, but which occur very rarely in inanimate materials. These other polarization modes are interfacial (inhomogeneous materials) and pre-polarized elements which occur readily in all animate tissues. It is known that the rest state of the human neural, cardiac, skeletal muscular and sensory systems are states of high polarization and are induced via ion ($K^+$, $Na^+$, $Ca^{++}$, etc.) transport across various membranes. Action potentials from this transport are used to maintain the systems' normal polarized state and to trigger the systems' activities via depolarization and follow-up rapid repolarization signals.

Dielectrophoresis has been practiced mostly using exclusively artificially-set-up external non-uniform electric field patterns in laboratories to dielectrically separate individual ($\mu$m size) inanimate, inorganic particles or $\mu$m size living cells (see, H. A. Pohl, *Dielectrophoresis*, Cambridge University Press (1978) and H. A. Pohl, *Electrostatics and Applications*, Chapters 14 and 15, A. D. Moore (Editor), Interscience Press (1973) and T. B. Jones, *Electromechanics of Particles*, Cambridge University Press (1995)). The problems of this prior art in trying to observe the dielectrophoresis force and torque effects in meter-size ensembles of tens of billions of $\mu$-size vertebrate cells coupled biochemically and working in concert as an animate entity are overcome by utilizing naturally-occurring electric field spatial gradient patterns, in particular the largest electric field spatial gradient pattern occurring in vertebrates, the one associated with vertebrate's beating heart, illustrated by the electrocardiogram (ECG). Table I lists the electro-physiology events in human heart beat cycles forming ECG's. A vertebrate is any animal having a backbone and some form of heart (one or more chambers) with a characteristic ECG.

FIG. 1 shows a human heart including right atrium 11, right ventricle 12, left atrium 13 and left ventricle 14. FIG. 2 shows the dipolar voltage and electric field patterns of the human heart. Curves (a) 21 and (b) 22 are the positive and negative isopotential lines. The curves (c) 23 are the resulting non-uniform electric field lines. FIG. 3 shows cardiac muscle or conduction cell membrane 31, through which various ions 32 (sodium and potassium) diffuse to form the polarized membrane resting state 33 and the depolarized activated state 34, the states being electrically linked and characterized by the action potential curve 35. FIG. 4 shows electro-physiology of the human heart. Sequential action potential curves are superimposed from the heart key action centers—sinus node 41, atrial muscle 42, A-V node 43, common bundle 44, bundle branches 45, Purkinje fibers 46, and ventricular muscle 47—to produce ajoint waveform 48 called an electrocardiogram (ECG). FIG. 5 shows a detailed normal ECG with characteristic waveform features—P 51, P-R interval 52, P-R segment 53, QRS spike 54, QRS interval 55, S-T segment 56, S-T interval 57, T 58, U 59 and the Q-T interval 50. FIG. 6 shows the moving depolarization vector at key electrical events in the 600 ms human cardiac heartbeat cycle—atrial depolarization at 80 ms 61, septal depolarization at 220 ms 62, apical depolarization at 230 ms 63, left ventricular depolarization at 240 ms 64, late ventricular depolarization at 250 ms 65, ventricles depolarized at 350 ms 66, ventricular repolarization at 450 ms 67, ventricles repolarized at 600 ms 68. The QRS spike waveform feature in the ECG is by far the largest electric field and has the greatest spatial gradient (across the left ventricular membrane wall).

SUMMARY OF THE INVENTION

The present invention detects the presence of various entities using an electrokinetic effect known as dielectrophoresis. As discussed above, a primary use of the present invention is detecting and locating animate entities such as human beings that are obscured from sight. The electrokinetic effect used by the present invention, dielectrophoresis, is one of five known electrokinetic effects, (the other four being electrophoresis, electro-osmosis, Dorn effect, and streaming potential), and describes the forces affecting the mechanical behavior of initially neutral matter that is dielectrically polarized by induction via spatially non-uniform electric fields. The spatial non-uniformity of an electric field can be measured by the spatial gradient of the electric field.

The dielectrophoresis force depends non-linearly upon several factors, including the dielectric polarizibility of the surrounding medium (air plus any intervening walls, trees, etc.), the dielectric polarizibility and geometry of the initially neutral matter (the device's antenna and other component parts of the device), and the spatial gradient of the square of the human target's local electric field distribution as detected at the device's antenna and other component parts. The dielectrophoresis force is produced by the spatial gradient of the target's field, which induces a polarization charge pattern on the device's antenna and other component parts, and this force is a constant direction seeking force always pointing (or trying to point) the device's antenna and other component parts toward the maximum in the three-dimensional non-uniform electric field squared spatial gradient pattern uniquely exhibited by a predetermined entity type.

This constant-direction-seeking force is highly variable in magnitude as a function of the angular position and radial position of the entity-to-be-located (like a human target) with respect to the device's antenna and other component parts of the device, and upon the effective dielectric polarizibilities of the intervening medium (like air) and of the materials used in the device's antenna and other component parts. The following equations define the dielectrophoresis forces wherein Equation 1 shows the force for spherical initially neutral objects (spherical antenna and the device's other component parts), and Equation 2 shows the force for cylindrical initially neutral objects (cylindrical antenna and the device's other component parts).

$$F = 2(\pi a^3) \in_0 K_1 (K_2-K_1)/(K_2+2K_1) \nabla |E_0|^2 \qquad \text{Equation 1}$$

$$F = L/a(\pi a^3) \in_0 K_1 (K_2-K_1)/(K_2+K_1) \nabla |E_0|^2 \qquad \text{Equation 2}$$

Where:

F is the dielectrophoresis force vector detected by the antenna and the device's other component parts;

a is the radius of the sphere or cylinder;

L is the length of the cylinder (L/a is the so-called axial ratio);

$\in_0$ is the permittivity constant of free space;

$K_2$ is the dielectric constant of the material in the sphere or cylinder;

$K_1$ is the dielectric constant of fluid or gas, (air) surrounding both the entity and the antenna and the device's other component parts;

$E_0$ is the electric field produced by the entity as detected by the antenna and the device's other component parts; and $\nabla$ is the spatial gradient mathematical operator.

The human-operated, hand-held locator device produces an observable torque as the antenna/locator detector device swings around the hand-held pivot point and acquires a local electric field spatial gradient max which gives via the dielectrophoresis force, a pinpoint line-of-bearing location of the human target. The detector specifiously locates the human heart's asymmetrical position in the human thoraic cavity, which is just left of the human target's sternum if the human target is front-facing the human operator and just right of the human target's sternum if the human target is back-facing the human operator. The size and extent of the observable torque depends on the angular, radial and vertical planar positions of the human operator. Despite human target movements, the antenna-locator detector is self-correcting, it reacquires in real time and locks-on to the spatial gradient signal and again pinpoints the living human target's heart. At sub-ULF and ULF frequencies utilized in the human heart electro-physiology, attenuation skin depths are extraordinarily large, so the detector can sense or detect through metals, earth, walls and all other vision-obstructing barriers.

The dielectrophoresis-based human heart line-of-bearing locators utilize living humans in two distinct roles as both target and operator for these devices. As to the living human's role as target, the ECG voltages and fields at the human body's thoraic cavity surface produced by the beating human heart were found first to mimic an average electric dipole distribution. More detailed ECG data led to an explanation via a more complex depolarization and repolarization vector moving in a ULF reproducible spatial sequence pattern throughout the heart's four chambers and other structures during a heart beat. This moving polarization vector (see FIG. 6) is the electric field and spatial gradient thereof that the line-of-bearing locator locks onto and real time tracks using the dielectrophoresis effect. See *Bioelectromagnetism*, R. Plonsey et al. (eds.), Oxford University Press (1995) and R. A. Rhoades, *Human Physiology*, Harcourt Brace Jovanioch (1992).

The electric field patterns and gradients generated by the heart's electric dipole would be expected to fall off rapidly with distance as the inverse square or cube of distance. But the human field patterns sensed by the line-of-bearing human locator between the human operator and the human target empirically behave as if they emanated from phase- and amplitude-coupled, partially (mostly)-coherent, partially-constructive interference ULF electric field generator producing an almost-distance-independent, highly-amplified electric field gradient pattern which interacts with the antenna/locator detection device via the dielectrophoresis effect to produce the force and observed torque even out to as far as 500 meters. This effect is not unlike the difference between a random thermonic emission light bulb (incoherent, phase- and amplitude-uncoupled, modest intensity, very distance-dependent light source) and an amplified stimulated emission laser light source (coherent, phase- and amplitude-coupled, very high intensity, almost distance-independent light source). Hence, the detection/locator system is able to "tune-in" to human signals even at very large distances.

The low-impedance connection between the universal ground (earth) and the two very high dielectric constant (semiconductive) human entities are believed to form some type of ULF resonant cavity type oscillator system. An analogy can be drawn with UHF microwave tuned-to-be-absorbed-by-water Klystron-like oscillators used in microwave ovens to cook food. Independent experimental evidence is available and growing to partially support this viewpoint on the almost-distance-independent effects seen with this invention's line-of-bearing dielectrophoresis force and torque human locator device. See *Biological Coherence and Response to External Stimuli*, H. Frohlich, Springer-Verlag Press (1988); *Coherent Excitations in Biological Systems*, H. Frohlich, Springer-Verlag Press (1983); *Electromagnetic Bio-Information*, F. Popp, et al., Urban Publ. (1979); W. Tiller et al. *Cardiac Energy Exchange Between People*, HeartMatch (1997); and W. Tiller, *Science and Human Transformation*, Pavior, Walnut Creek (1997).

It should be noted that the term "antenna" as used in this context includes, (in a very real sense), all of the components and the living human operator present in the device of the present invention. To this extent, the dielectric constant of the materials including living biological tissue (human operator) that make up the locator of the present invention all determine the overall value of $K_2$ in the above equations. These materials are not arranged in a uniform spherical or cylindrical shape, and therefore the exact value of $K_2$ and the exact functional relationship of $K_1$ and $K_2$ in a closed mathematical equation form accurately representing the real world locator device is difficult, if not impossible, to determine. In a practical sense, experimentation has shown (and is continuing to show) the types and placement of dielectric materials needed to produce maximum dielectrophoretic force and subsequent resulting torque, acceleration, vibration or any other measurable quantifiable manifestations of the force for precisely locating different types of entities. The following table lists some of the dielectric materials used in the locator ($K_2$ values) and/or surrounding (such as air, water, walls, etc.) the locator ($K_1$ values) and the dielectric constant for these materials.

| MATERIAL | CONSTANT (at ULF 10 Hz) |
| --- | --- |
| air | 1.0 |
| PVC | 3.0 |
| nylon | 4.0 |
| polyester | 5.5 |
| silicon | 12.0 |
| 2-propanol | 19.9 |
| water | 78.4 |
| n-maa | 191.3 |
| selenium | 1000 |
| $BaTiO_3$ | 4000 |
| $(CS_2)_n$ | 20,000 |
| metal | $\infty$ |
| lung | $3 \times 10^7$ |
| heart muscle | $7 \times 10^6$ |
| skeletal muscle | $1 \times 10^7$ |
| liver | $5 \times 10^7$ |
| fat (100 Hz) | $2 \times 10^5$ |
| kidney (10 kHz) | $5 \times 10^4$ |
| blood (10 kHz) | $3 \times 10^3$ |
| brain (100 kHz) | $4 \times 10^3$ |
| bone (100 Hz) | $4 \times 10^3$ |

The above discussion and equations concerning dielectrophoresis provide a rational explanation of the operating principles of the present invention that is consistent with all empirical observations associated with the present invention. These operating principles involve using the above mentioned forces to point an antenna and all other components attached to the device toward the maximum gradient of the local electric field, to thereby indicate the line-of-bearing direction toward an unseen entity.

In accordance with the invention, an operator holds the locator device in hand, and through a handle, the locator device is electrically and dielectrically connected to the operator. The operator is partially electrically grounded (through the operator's feet), and thereby the individual human operator body's capacitance (C) and resistance (R) to true ground are connected electrically to the handle of the locator device. Ranges for an individual entire human body's C have been measured as 100 pF to 400 pF and for individual human body's R have been measured as 0.03 KΩ to 1 MΩ. Thus, the generalized electrical parameter (the polarization charge pattern induced on the device by the electric field spatial gradient of the entity in this case, but also electric field, current and voltage) exponential decay time (=RC) constant range for the variety of human being bodies potentially acting as locator device operators is about 3 to 400 µ seconds. This decay time constant is greatly increased through an externally connected resistor of up to 5000 MΩ and inductor with an inductance up to 200 mH or a capacitor with a capacitance up to 56 mF, which results in an effective human operator's exponential decay time constant up to 1 to 10 seconds.

This enables dielectrophoretic forces caused by the induced polarization charges (bound, not free) pattern on the locator device's antenna and other component parts to be detected, replenished instantly with each new heartbeat and locked onto since the force is replenished faster than the induced polarization charge pattern on the device can decay away to true ground through the operator's body. This effect is called, and is using, the spatially self-correcting nature of the dielectrophoretic force (always pointing or trying to point to the maximum of an entity's electric field three-dimensional squared spatial gradient pattern).

The locator device is held in a balanced (two to three degrees tilt angle down from absolute) horizontal state, and the operator scans the locator device in a constant speed uniform linear motion back and forth. An antenna extends from the front of the locator device and is acted on by the aforementioned force. This force creates a subsequent resulting torque around a well defined pivot line, which is constant-direction-seeking and tends to make the locator device's antenna and the device's other component parts point toward the maximum spatial gradient of the square of the non-uniform electric field uniquely exhibited by any target human beings or other predetermined animate entity within the range of the locator device.

The effect creates a self-correcting action of the locator device when the human operator scans the device in a uniform motion to lock onto a target entity initially. The effect also creates an additional self-correcting action of the locator device to closely follow the radial and angular motions of an entity (to track and reacquire a target entity once the operator has initially locked onto a target entity). The self-correcting action of the locator device to reacquire a target occurs without any additional overt action on the part of the human operator, and the device thereby is operating independently of the human operator.

Four internal N-channel J-FETs (field effect transistors) are connected to the locator device's antenna and operate in their non-linear range to effectively change the antenna's length. Three of these FETs are arranged in modules that are equidistant from the antenna's longitudinal axis and are spaced 120 degrees apart. The fourth FET is arranged in a module below the axis and to the rear of the locator device. Three potentiometers are provided on the first three modules to adjust the current levels through the first three FETs and thereby tune the locator to point directly at a human being's body located at a precise known position as a reference target entity. The gain and frequency response of the fourth FET by virtue of the voltage pattern induced by the reference entity is adjusted by a six position switch connected to the base of an NPN transistor. By changing the frequency response of the locator device, the device is tuned to reject the higher frequency electromagnetic signals and noise from all external sources, including those sources associated with the human operator in order for the locator device to interact with and respond to only the three-dimensional non-uniform electric field squared spatial gradient pattern exhibited uniquely by a predetermined entity type.

While scanning the locator device in a constant uniform motion back and forth in front of a known entity (such as a human, if the target is a human being), the operator changes the six position switch until a maximum force and subsequent resulting torque is detected and used to aim the antenna and the device's other component parts toward the target entity. After selecting the setting of the six position switch, the operator adjusts the gain of the first three FETs until the locator device points or tries to point directly at the target entity. For different entities, different dielectric materials are used in the locator device's antenna and its other component parts. Examples of detectable entities include human beings, other mammals as well as other biological entities such as birds, reptiles, amphibians and other vertebrae. Continued research on the instrument has yielded positive results in the instrument's ability to be tailored both as a geometrical design and with respect to materials and other components of construction to specifically detect a variety of different target entities.

Accordingly, it is an objective of the invention to provide an accurate method of locating the direction and position of a target animate entity relative to the instrument's human operator. It is another objective of the invention to provide improved elements and arrangements thereof in an apparatus for the purposes described which is inexpensive, dependable and fully effective in accomplishing its intended purposes.

BRIEF DESCRIPTION OF THE DRAWINGS

These and other objectives of the present invention will become readily apparent upon further review of the following specification and drawings, wherein.

DETAILED DESCRIPTION OF PREFERRED EMBODIMENTS

Figure 1:
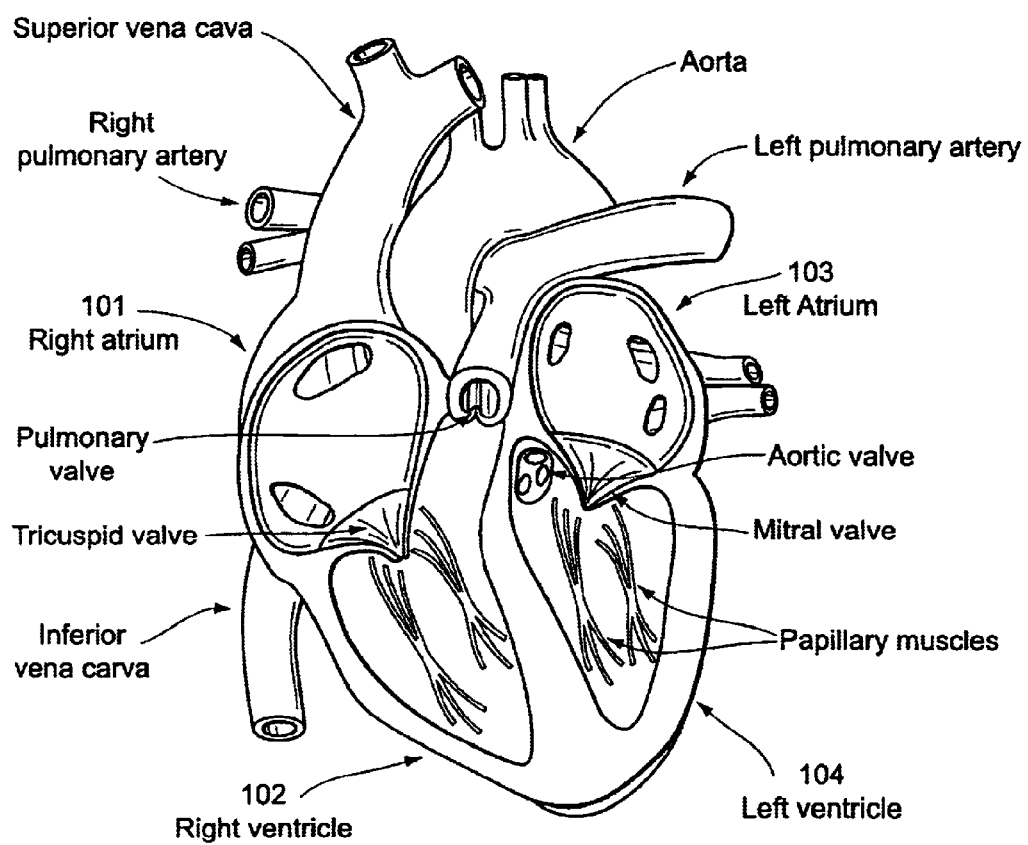
FIG. 1 is a schematic drawing of the human heart anatomy.
Figure 2:
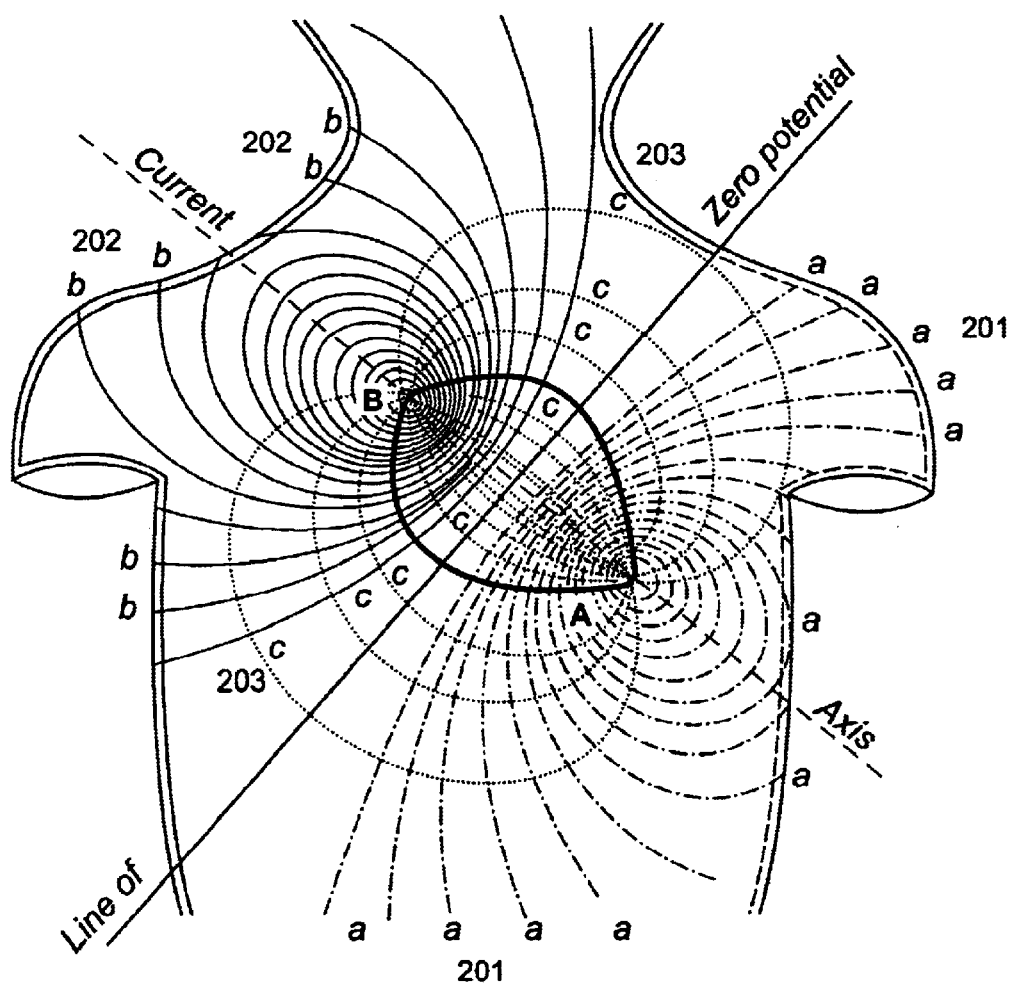
FIG. 2 is a schematic drawing of the human heart effective, average electric dipole field and voltage patterns manifested at the surface (skin) of the thoracic (lung, heart and rib cage) cavity.
Figure 3:
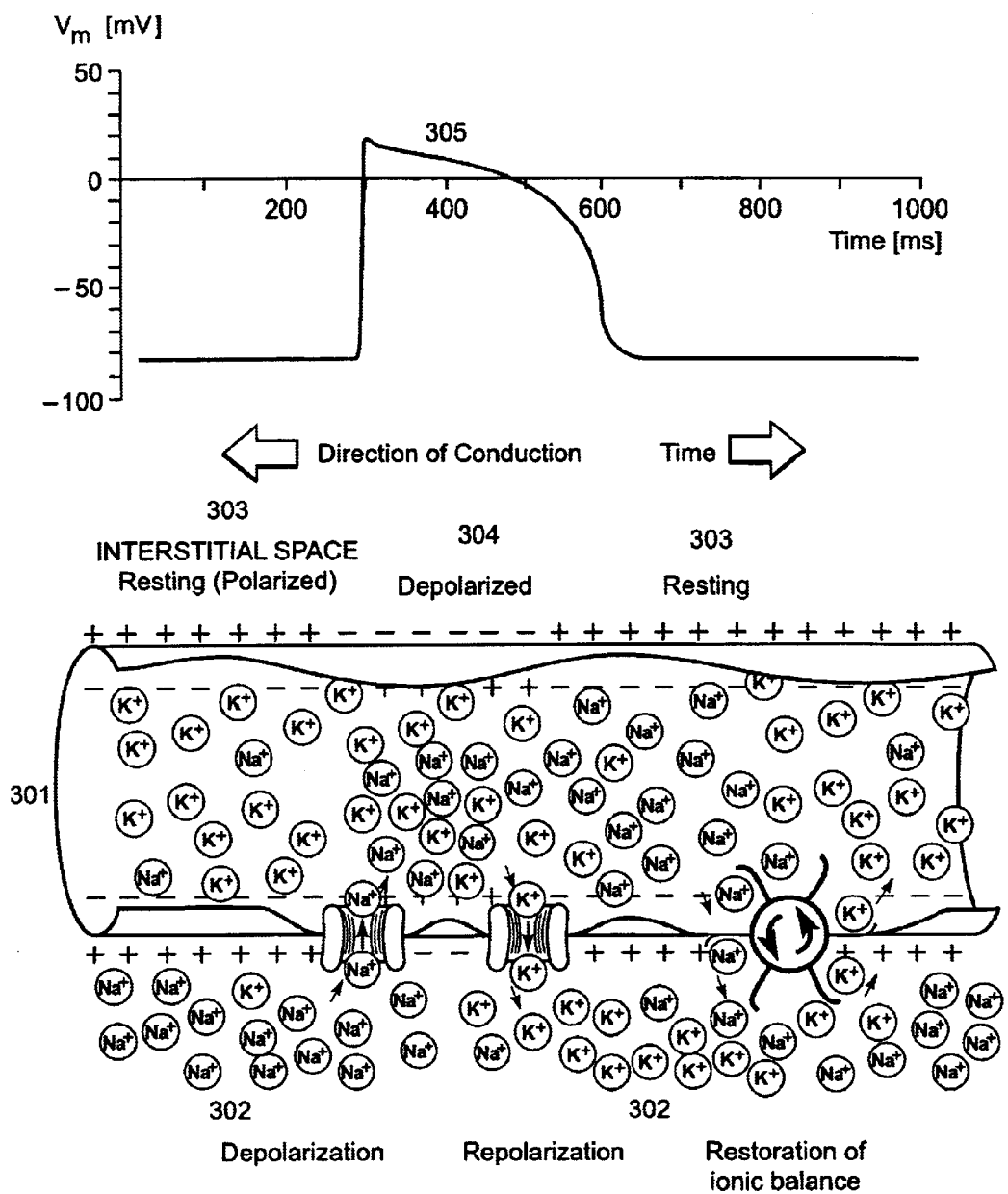
FIG. 3 is a schematic drawing of the action potential of a human cardiac muscle cell membrane and the biochemical diffusion of potassium and sodium ions across the membrane from an electrically highly polarized resting state to a depolarized working state and a repolarized resting state.
Figure 4:
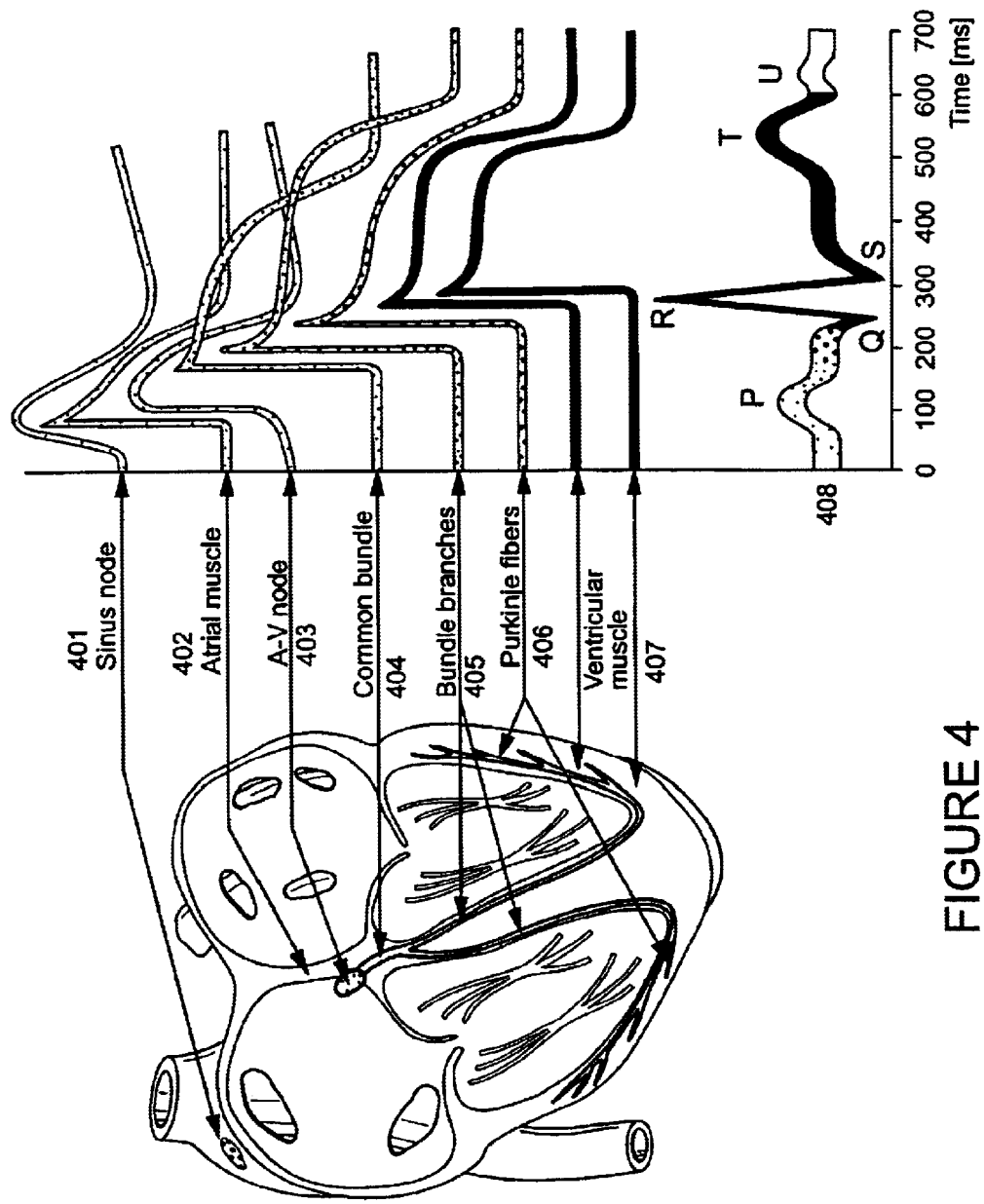
FIG. 4 is a schematic drawing of the electro-physiology sequencing occurring during one human heart beat cycle.
Figure 5:
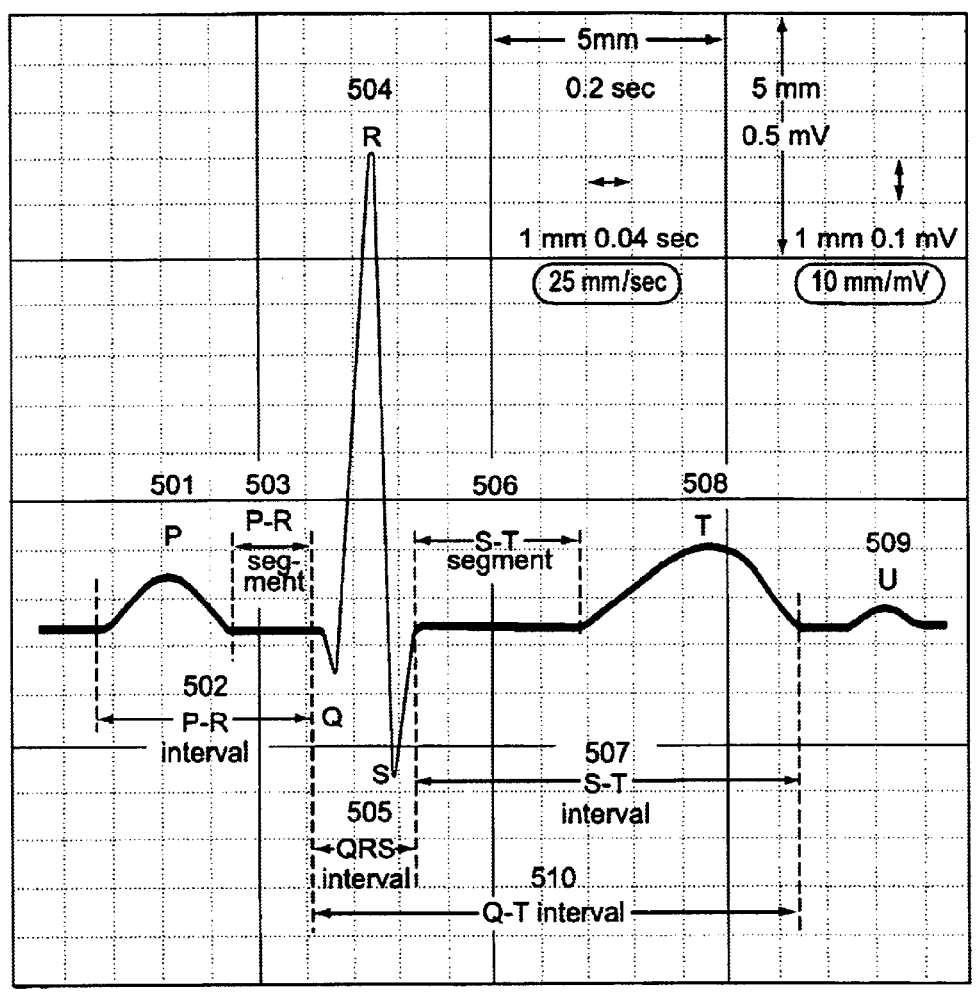
FIG. 5 is a graph of the normal human electrocardiogram (ECG)
Figure 6:
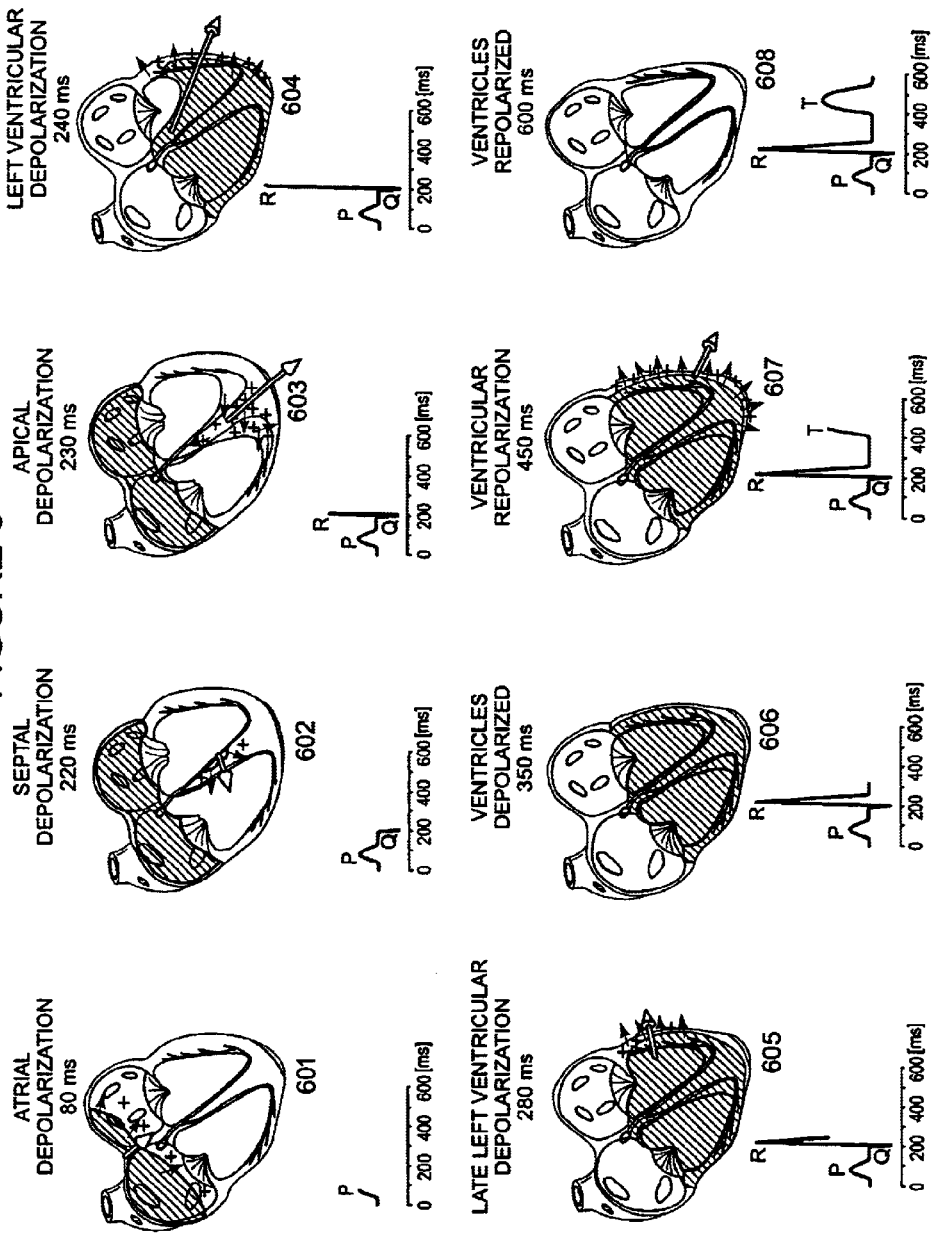
FIG. 6 graphs the moving depolarization and repolarization vector in a human ECG.
Figure 7:
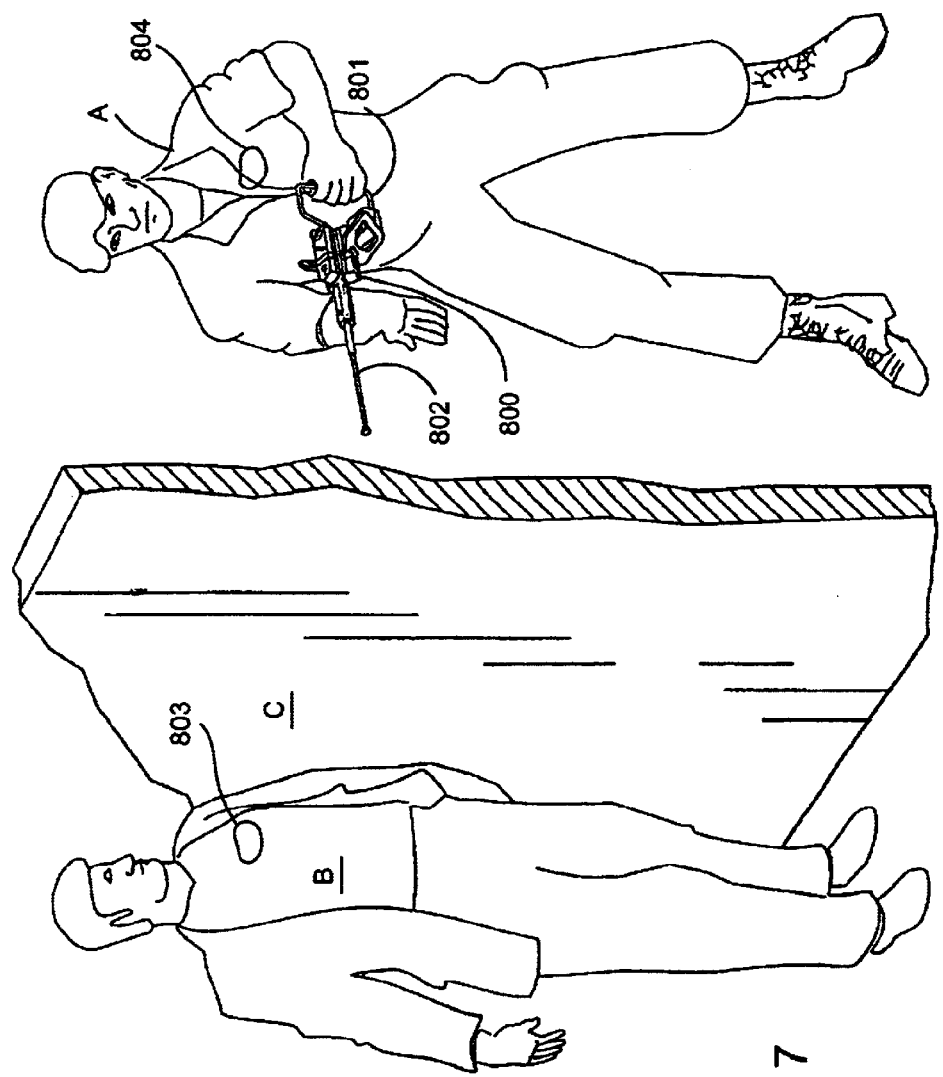
FIG. 7 is an environmental view of the locating device being used by a first person to locate a second, hidden person in accordance with the present invention.

The device according to the present invention is shown as locator device 100 in FIG. 7. A human operator A is shown using the locator device to detect the presence of a second human being B who is visually obscured behind a wall C. The handle 101 of the locator 100 is in electrical and dielectric contact with the operator's hand, and the antenna 102 and the locator device's other component parts are acted on by the aforementioned forces. By holding the locator 100 in a nearly horizontal level (two to three degrees tilt angle down from absolutely level) position and scanning the locator device 100 in a uniform and constant speed linear motion back and forth, the operator A detects a self-correcting constant-direction-seeking force, and the subsequent resulting torque upon the antenna 102 and the locator device's other component parts cause the locator device to torque, pivot and point toward the direction and location of the visually obscured second human being B.

Figure 8:
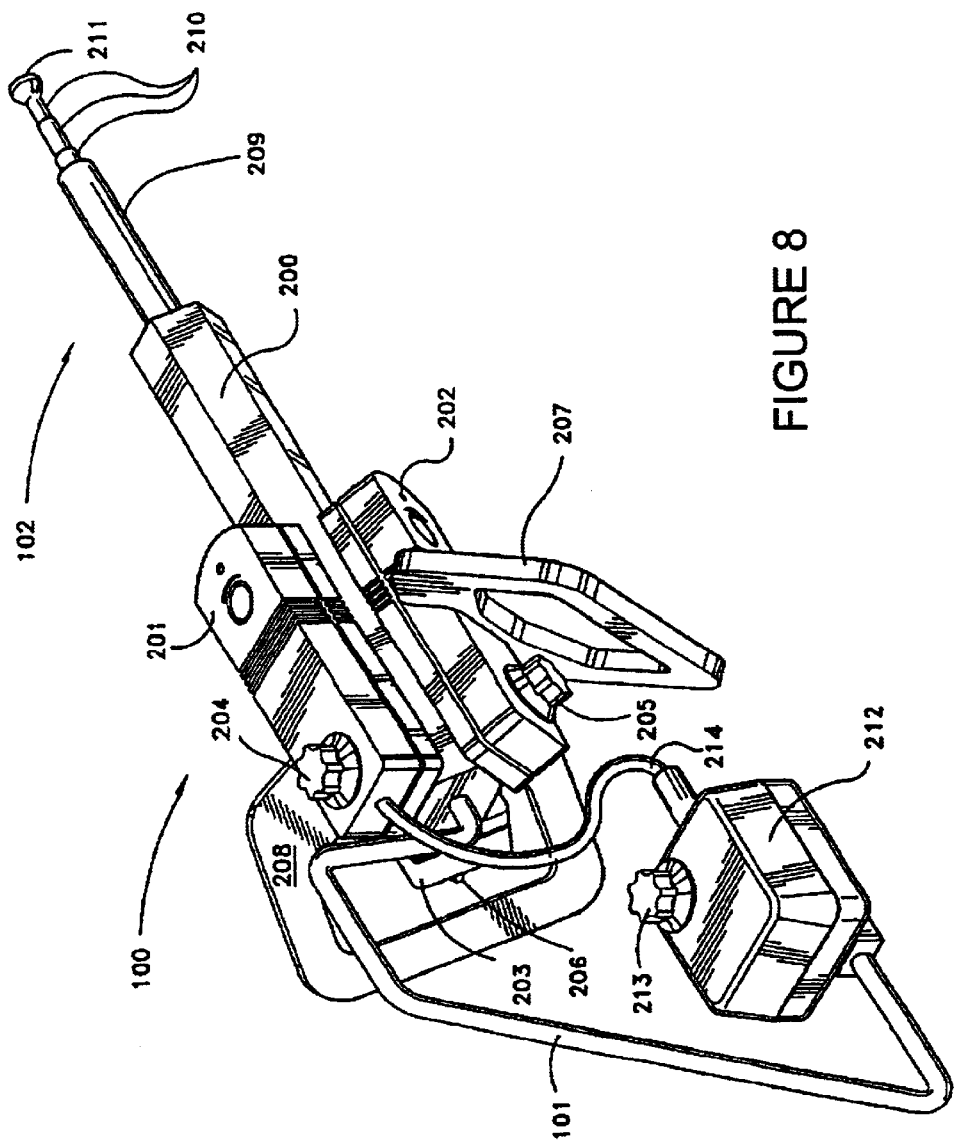
FIG. 8 is a perspective view of the locating device in accordance with the present invention.
Figure 9:
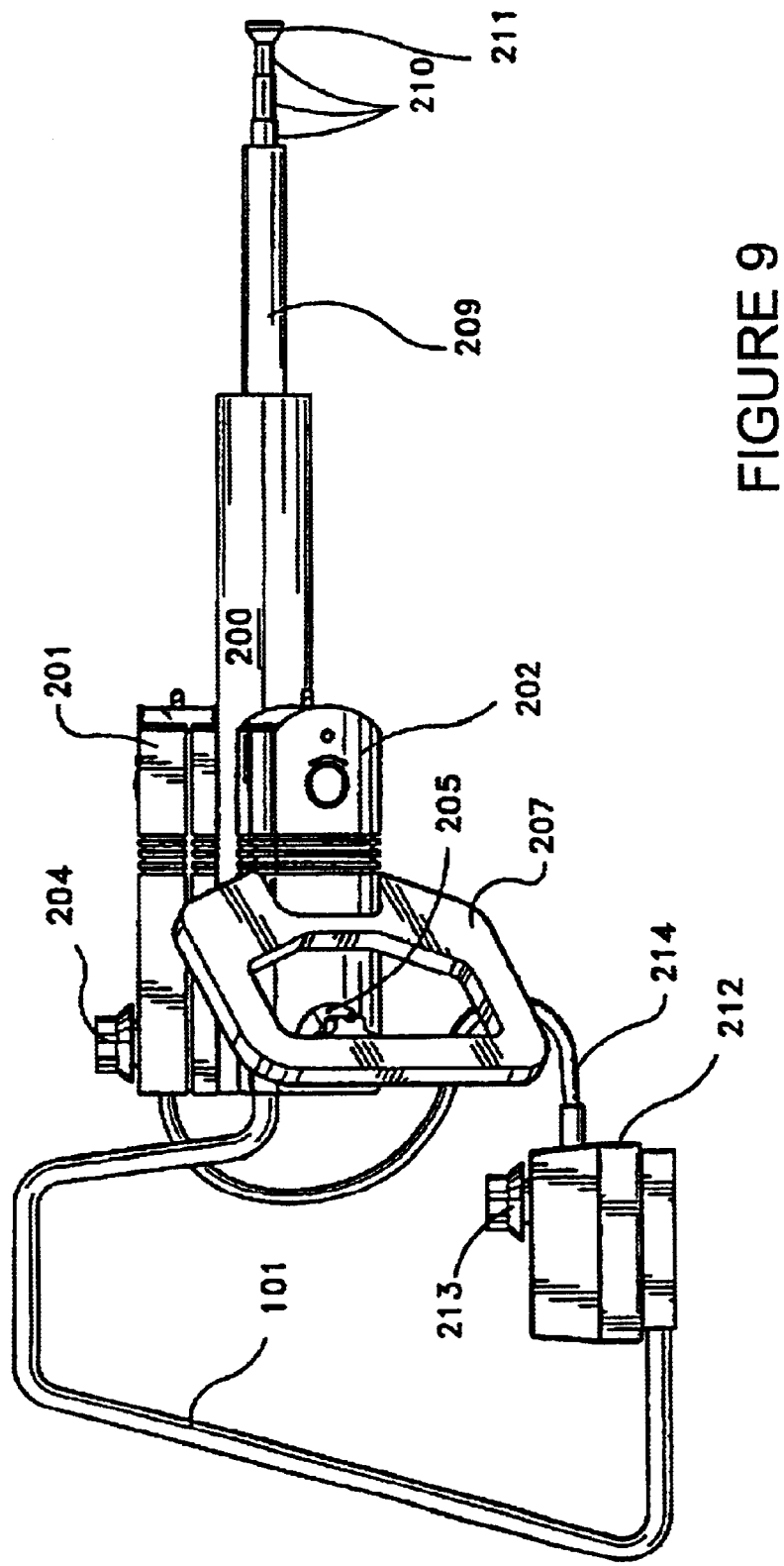
FIG. 9 is a right side view of the locating device shown in FIG. 8.
Figure 10:
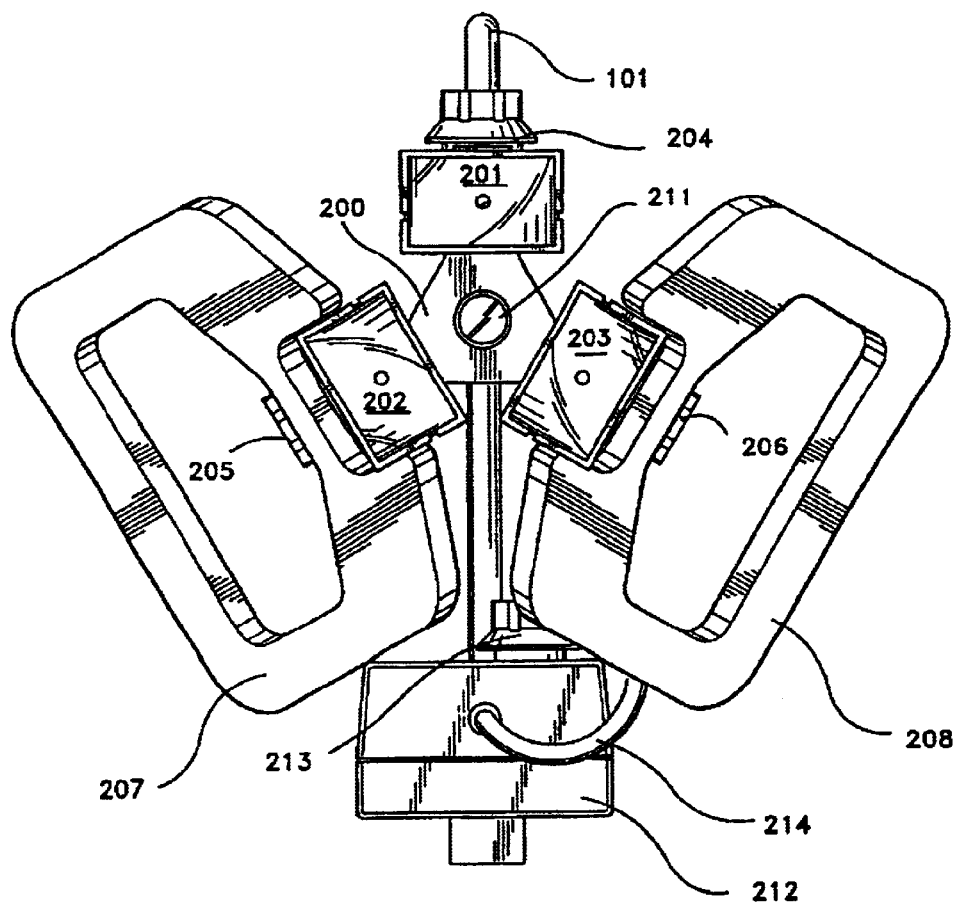
FIG. 10 is a front view of the locating device shown in FIG. 8.

The details of the exterior of the locator 100 can be seen in FIGS. 8–10. The antenna 102 includes a rear portion 209 made of nylon or similar material, telescoping sections 210, and an end knob 211. The antenna 102 protrudes from a central dielectric housing 200 in a coaxial arrangement. The antenna telescoping sections 210 and the antenna rear portion 209 can be moved singly or jointly to adjust the axial ratio of the locating device 100 to obtain optimum torque-induced pivoting response of the locator 100. The enhancement is obtained by changing the length of the antenna and/or changing the exact relative position of the whole antenna compared to the positions of the other device components. The antenna 102 does not necessarily have to be of the telescoping type, nor made of metal material, and can be a one piece rigid or flexible type antenna made from metal or plastic materials. Furthermore, as all of the components of the locator device 100 effectively act as an antenna, the locating device operates as described without the antenna 102 installed, although the forces produced are greatly reduced.

Attached to the central dielectric housing 200 are three modules 201, 202, 203. The top module 201 is mounted directly over the common axis of the antenna 102 and the central dielectric housing 200 and in line with this axis. The lower right module 202 and lower left module 203 are spaced 120° apart from each other and the top module 201 and are also in line with the axis. Each module 201, 202 and 203 has a variable resistor control knob 204, 205 and 206, respectively. The lower right module 202 and lower left module 203 include parabolic antennas 207 and 208, respectively, both of the parabolic antennas being attached to their respective module in a swept back position. The handle 101 is formed from a metal rod that protrudes coaxially from the central dielectric housing 200. The handle 101 bends upward, extends horizontally for a short distance, bends downward to form a handle, and then bends forward to provide a support for a bottom tuning module 212. The bottom tuning module 212 includes a variable resistor control knob 213 and a cable 214 that attaches to the top module 201. The modules 201, 202, 203 and 212 form in part a selective polarization filter or unit that serves as a matching bridge between the human detector operator and the opposite polarized detector component to generate the opposite polarization pattern. An example of an alternative polarization matching filter is disclosed in co-pending application Ser. No. 08/840,069, the disclosure of which is hereby incorporated by reference.

Figure 11:
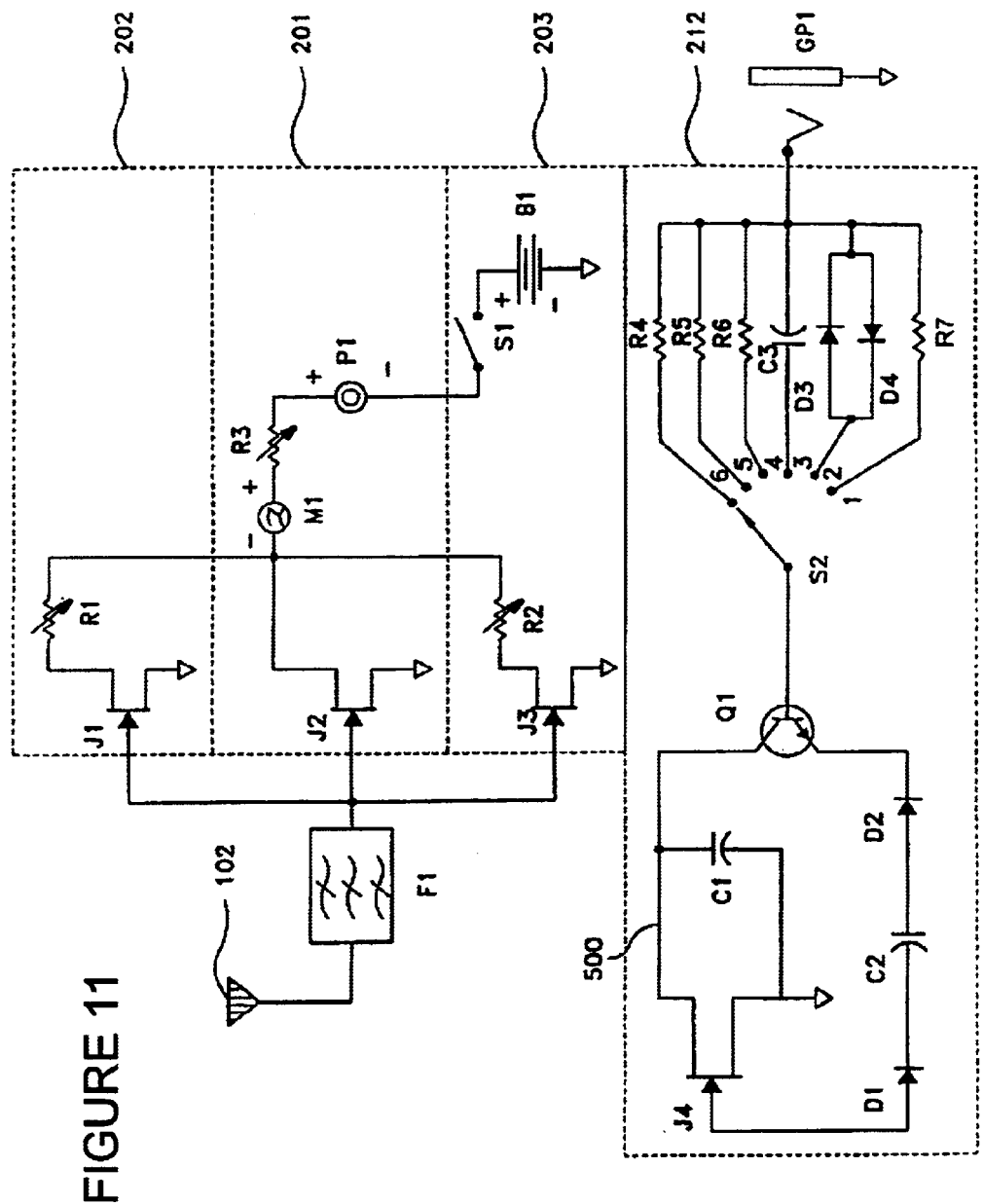
FIG. 11 is a schematic diagram of the three main modules and the bottom tuning module of the locating device of FIG. 8.

The electronic circuitry for the locator device 100 is shown in FIG. 11. The antenna 102 is connected to an optimal low pass filter F1, which removes all high frequency signals and noise from all external electromagnetic sources, including those from the human operator A himself. The details of the electronic circuitry and the geometrical design and materials of construction used in the locator device 100 are chosen so as to tailor the locator device 100 for a predetermined entity type. The output from the optimal low-pass filter F1 is fed to the gate of the three N-channel field effect transistors, (FETs). The three FETs act as amplifiers and are housed one each in the three modules. The lower right module 202 contains FET J1 and a 0–100 k$\Omega$ variable resistor R1, the top module 201 contains FET J2, a DC ammeter M1, 0–100 k$\Omega$ variable resistor R3, and a piezo buzzer P1, and the lower left module 203 contains FET J3, a 0–100 k$\Omega$ variable resistor R2, an on/off switch S1 and a 9-volt battery B1.

Variable resistors R1 and R2 adjust the current gain of FETs J1 and J3, respectively. By adjusting the gain of these FETs, the effective electrostatic effect on these devices is balanced relative to FET J2. The overall gain of FETs J1, J2 and J3, is adjusted by 0–100 k$\Omega$ variable resistor R3. The DC ammeter M1 is provided to indicate the combined current flow through all three FETs. In addition, the piezo buzzer P1 provides an audio output whose frequency increases as the current through the circuit increases. The battery B1 provides the required supply voltage (preferably nine volts) to operate the circuit, and the switch S1 provides a means for turning the amplifiers J1–J3 on and off.

The bottom module 212 contains the necessary circuitry for increasing the human operator's electrical parameter decay (RC) time constant, from $\mu$ seconds as occurs naturally to seconds as explained previously, needed to capture and lock onto the dielectrophoretic force exhibited by a target entity and the subsequent resulting torque, acceleration, vibration or any other measurable, quantifiable manifestation of the force detected by the locator device 100. A ⅛ inch grounding jack GP1 is used to provide a ground to the circuit by inserting a mating shorting plug into the jack GP1. Once inserted, the mating plug (via the jack GP1) provides a ground potential via the reference entity RE to each of 3.3 k$\Omega$ resistor R4, 22 k$\Omega$ resistor R5, 100 k$\Omega$ resistor R6, 0.01 mF capacitor C3, clipping diodes D3 and D4, and 10 M$\Omega$ resistor R7 of a six-position selector switch S2. The six-position selector switch S2 can be moved to one of six positions to connect the base of an NPN transistor Q1 to one of the above components. The NPN transistor Q1 makes up part of a tunable circuit that also includes an N-channel FET J4, a first 0.01 $\mu$F capacitor C1, a first diode D1, a second diode D2, an electrical line 500, and a second 0.01 $\mu$F capacitor C2. By inserting or removing the shorting plug into the jack GP1 and changing the position of the switch S2, the gain of the transistor Q1 can be adjusted, and the overall frequency response of the tuned circuit in the bottom module 212 can be changed for maximum response.

The extraordinarily high ULF dielectric constants for living tissues, given in the previous table, allows the human operator's electrically grounded body to directionally distort, concentrate or focus the non-uniform electric field pattern emanating from the living human target. This action greatly increases the electric field flux density near the locator device. This field line concentrating increases the torque-producing dielectrophoresis force and results in an effective increase in the amplification or gain of the locator device as the operator samples the electric flux density as the device is moved in a uniform constant speed linear motion back and forth to initiate torque and lock-on.

The torque-produced pivoting response can be further increased by adding additional circuit elements such as capacitors, resistors and/or inductors to the circuit already described with reference to FIG. 11. For example, a resistor and a capacitor may be coupled in parallel with the top module 201, or a resistor and an inductor may be coupled in parallel with the top module 201. These circuit elements decrease the response time of the locator device. Preferred value ranges for the elements are up to 56 mF for the capacitors, up to 5,000 MΩ for the resistors and up to 200 mH for the inductors. These circuit elements serve to modify and optimize the device's polarization response and decay time constants.

As stated earlier, all of the components in FIG. 11 act as antenna extensions that increase the dielectrophoretic force and the subsequent resulting torque that is detected by the locator device 100. Every human being, as a locator device operator, has a different capacitance (C) and resistance (R) resulting in a low exponential decay time constant (=RC) for capturing and locking onto the dielectrophoretic force and the subsequent resulting torque. By adjusting R1–R3 and S2, the individual human operator and the locator device 100 can be jointly tuned and optimized to detect the maximum dielectrophoretic force and subsequent resulting torque for the specific human being operating the locator device 100. This is accomplished by using a reference entity (such as a visible human being) and adjusting S2 and R3 until the maximum dielectrophoretic force and subsequent resulting torque are detected by the individual human operator. Once the position of S2 has been determined, the operator notes the direction the antenna is pulled relative to the reference entity. If this direction is not exactly toward the reference, R1 and R2 are adjusted until the torque on the locator device 100 tends to point the antenna 102 directly toward the reference entity. After the locator device 100 is tuned and optimized, unobserved entities of the same type as the reference entity can be easily located by the device.

Figure 11A:
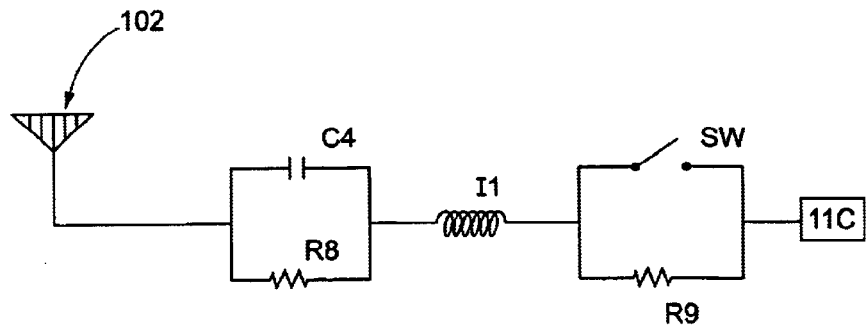
FIG. 11A illustrates an alternative detection/meter circuit according to the invention.

Of course, alternative arrangements for the electronic circuitry including functionally equivalent circuits may be utilized, and the invention is not meant to be limited to the arrangement illustrated in FIG. 11. For example, in one alternative arrangement, with reference to FIG. 11A, the antenna 102 is coupled to a parallel RC circuit including for example a 54 MΩ resistor R8 and a 330 pFd capacitor C4, which in turn is coupled in series with an inductor I1 having an inductance of, for example, 1 mH. The circuit elements R8, C4 and I1 serve to increase the human operator's electrical parameter decay time constant and create a quick response to the detected electric field. The RC circuit also provides an ultra-low bandpass filter that effectively eliminates noise and clutter at higher electrical frequencies.

Figure 11B:
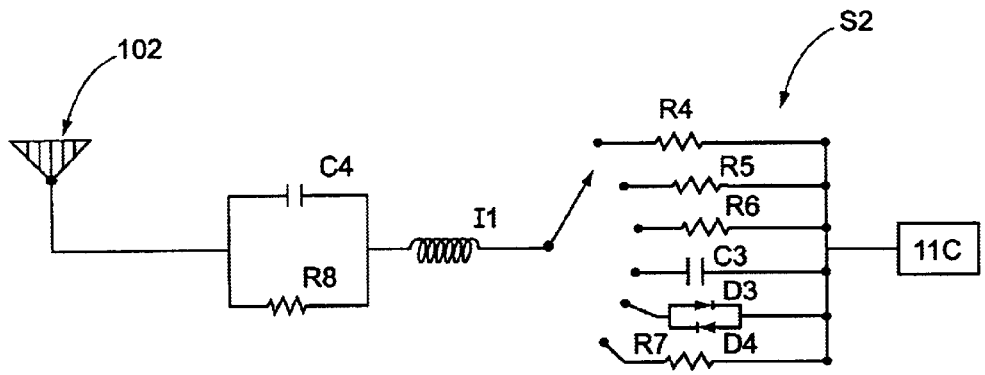
FIG. 11B illustrates another alternative detection/meter circuit according to the invention.

In this arrangement, the circuit elements are coupled with a mode selection circuit including for example a 1 kΩ resistor R9 that can be shorted across an exterior mode switch SW for increasing the resultant torque force. FIG. 11B illustrates an alternative mode selection circuit including elements R8, C4 and I1 coupled with the six-position selector switch S2 discussed above with respect to FIG. 11.

Figure 11C:
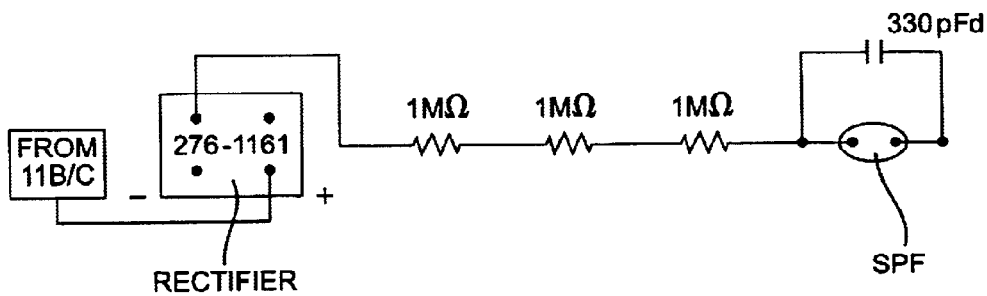
FIG. 11C illustrates a circuit element according to the invention including the selective polarization matching filter.

It has been discovered that the addition of a serially connected arrangement illustrated in FIG. 11C, including a 4-pin silicon bridge rectifier such as, for example, a Radio Shack part #276-1161, coupled in series with three 1 MΩ resistors continuing to an arrangement including a capacitor of, for example, 330 pFd capacitance connected in parallel with the selective polarization filter SPF of the invention significantly enhances the performance of the locator. The arrangement shown in FIG. 11C is connected to the mode selection portions shown in FIGS. 11A and 11B, for example.

Figure 12:
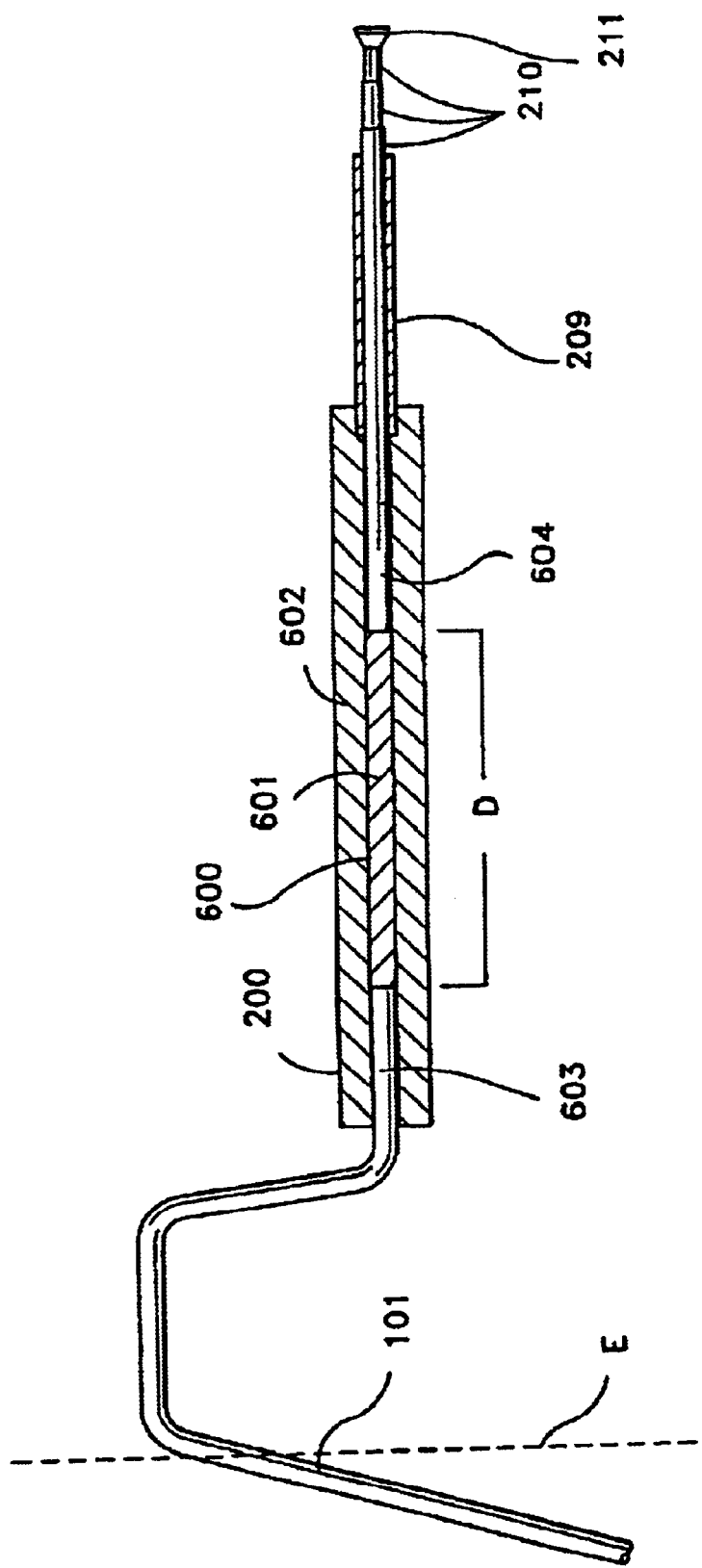
FIG. 12 is a cross-sectional view along the length and through the center of the locating device of FIG. 8.
Figure 13:
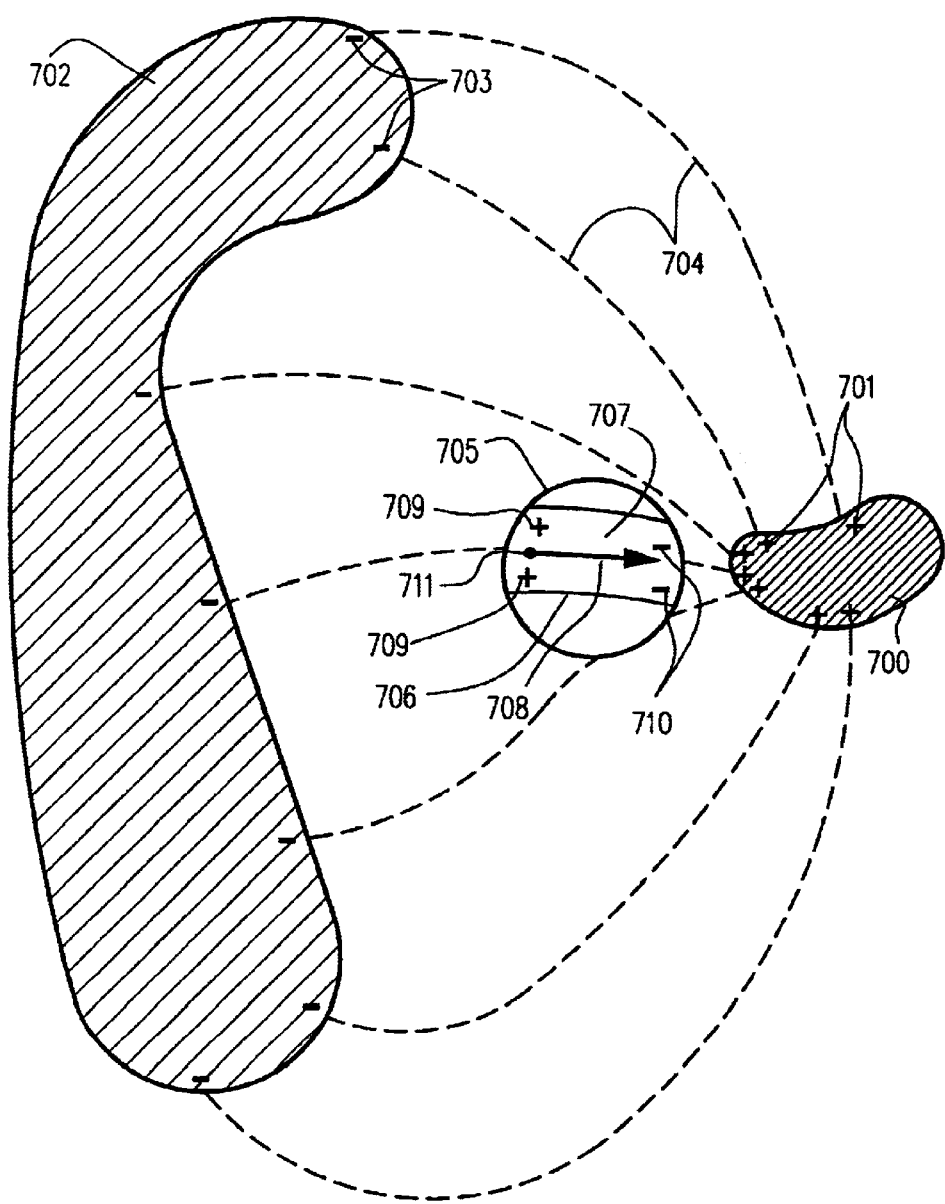
FIG. 13 is a schematic drawing of an entity, a ground plane, the device of the present invention and the entity's polarization electric field lines.

The interior of the central dielectric housing 200 is shown in FIG. 12. One end 604 of the telescoping antenna 102 extends into the front end of the housing 200, while an end 603 of the handle 101 extends into the rear end of the housing 200. A cavity 600 is filed with a first dielectric material 601 that surrounds both the interior end 604 of the telescoping antenna 102 as well as the interior end 603 of the handle 101. Around this cavity 600 is a second dielectric material 602 that defines the shape of the cavity 600 and also contacts the interior end 604 of the telescoping antenna 102 as well as the interior end 603 of the handle 101 near the point where end 604 and end 603 exit the housing 200. The device's handle 101 with the operator's hand defines a pivot line E around which the dielectrophoretic force produces the subsequent resulting torque, acceleration, vibration or any other measurable, quantifiable manifestation of the force. The ends 604 and 603 are separated by a distance D, which distance is human-operator-specific and also affects the overall sensitivity and response of the locator device 100 with respect to maximum detectable force and torque.

While the specific dielectric materials for maximizing the torque effect on the antenna for different entities are still being researched, dielectrics have been found that produce a usable torque for precisely locating animate entities such as human beings. In particular, the handle 101 and the antenna 102 preferably contain some metal, material 601 is air, material 602 is PVC, and the rear portion 209 of the antenna is nylon. In addition, the circuitry in modules 201, 202, 203 and bottom module 212 is encapsulated in PVC, while the modules themselves, housing 200, as well as the parabolic antennas 207 and 208, are also made of PVC. When these materials are used, an effective dielectrophoretic force and the subsequent resulting torque are detected by the antenna 102 and the device's other component parts to precisely locate the presence of human beings. Dielectric material 601 may alternately be selected from the following materials with varying levels of resulting torque: water (distilled, deionized), glycerol, (di)ethylene, triethylene glycol, 2-ethyl-1,3-hexanediol, γ-butyrolactone, dimethylpropionamide, di-methyl sulfoxide, methanol, ethanol, 2-propanol, 2-methyl-2 propanol, barium titanate, lead titanate, lead zirconate titanate, and highly-interfaced biomimitic keratinized materials. Device housing material 602 can be made from polyvinyl chloride, polyurethane, or any one or more of well-known engineering plastics.

FIG. 12 shows a target entity of interest 700 and a surrounding ground plane 702. The entity's polarization charges 701 produce non-uniform electric field lines 704 that have a unique spatial pattern as shown. The non-uniform electric field lines 704 also have a unique spatial gradient pattern (not shown). The non-uniform electric field lines 704 terminate on the surrounding ground plane 702 and induce opposite polarization charges 703 thereon. An initially neutral matter or medium 705, such as the device of the present invention, is shown amidst the non-uniform electric field lines. The neutral matter 705 includes a cavity 706 filled with a specific dielectric material 707. The non-uniform electric field lines induce polarization charges 709 and 710 in the dielectric material 707. The neutral matter 705 also contains protuberant antennas 708 that are formed from a specific dielectric material and are in direct contact with the cavity 706 and the dielectric material 707. The protuberant antennas 708 form a pivot line 711 that is perpendicular to the plane containing FIG. 12. The dielectrophoretic force manifests itself as an easily detected torque motion of the antenna 708 about the pivot line 711.

Obvious extensions of the ideas presented in this invention can be used to detect other animate entities including member species of the animal kingdom including mammalia other than homo-sapiens, aves (birds), reptilia (reptiles), amphibia (frogs and other amphibians), etc.

It is to be understood that the present invention is not limited to the embodiments described above, but encompasses any and all embodiments within the scope of the following claims.

TABLE I

Electric events in the heart

| Location in the heart | Event | Time [ms] | ECG-terminology | Conduction velocity [m/s] | Intrinsic frequency [1/min] |
|---|---|---|---|---|---|
| SA node | impulse generated | 0 | | 0.05 | 70–80 |
| atrium, | | | | | |
| Right | depolarization* | 5 | P | 0.08–1.0 | |
| Left | depolarization | 85 | P | 0.08–1.0 | |
| AV node | arrival of impulse | 50 ⎫ | P–Q | 0.02–0.05 | |
| | departure of impulse | 125 ⎭ | interval | | |
| bundle of His | activated | 130 | | 1.0–1.5 | |
| bundle branches | activated | 145 | | 1.0–1.5 | |
| Purkinje fibers endocardium | activated | 150 | | 3.0–3.5 | |
| Septum | depolarization | 175 ⎫ | | 0.3–(axial) | 20–40 |
| Left ventricle epicardium | depolarization | 190 ⎬ | QRS | 0.8 | |
| Left ventricte | depolarization | 225 ⎭ | | (transverse) | |
| Right ventricle epicardium | depolarization | 250 | | | |
| Left ventricle | repolarization | 400 ⎫ | | | |
| Right ventricle endocardium | repolarization | | T | 0.5 | |
| Left ventricle | repolarization | 600 ⎭ | | | |

*Atrial repolarization occurs during the ventricular depolarization: therefore it is not normally seen in the electrocardiogram.

What is claimed:

1. A locating device comprising a polarization unit that detects a polarization charge pattern by a manifested dielectrophoresis force in accordance with a spatially non-uniform electric field exhibited by a target entity.

2. A locating device according to claim 1, further comprising a pattern decay circuit operatively coupled with said polarization unit, said pattern decay circuit increasing a decay time constant of the polarization charge pattern.

3. A locating device according to claim 2, wherein said pattern decay circuit comprises a resistor and a capacitor coupled in parallel with said polarization unit, said resistor and capacitor modifying and optimizing said decay time constant.

4. A locating device according to claim 3, wherein said resistor has a resistance of up to 5000 MΩ, and wherein said capacitor has a capacitance of up to 56 mF.

5. A locating device according to claim 2, wherein said pattern decay circuit comprises a resistor and an inductor coupled in parallel with said polarization unit, said resistor and inductor modifying and optimizing said decay time constant.

6. A locating device according to claim 5, wherein said resistor has a resistance of up to 5000 MΩ, and wherein said inductor has an inductance of up to 200 mH.

7. A locating device according to claim 1, wherein said polarization unit comprises a housing formed of a first dielectric material and defining a cavity therein.

8. A locating device according to claim 7, wherein said first dielectric material is polyvinylchloride (PVC).

9. A locating device according to claim 7, wherein said first dielectric material is polyurethane (PUT).

10. A locating device according to claim 7, further comprising a second dielectric material disposed in said cavity.

11. A locating device according to claim 10, wherein said second dielectric material is air.

12. A method for locating a target entity with a locating device, the method comprising detecting a polarization charge pattern by a manifested dielectrophoresis force in accordance with a spatially non-uniform electric field exhibited by the target entity.

13. A method according to claim 12, further comprising increasing a decay time constant of the polarization charge pattern.

14. A method according to claim 13, wherein said increasing step comprises modifying and optimizing the decay time constant.

15. A method according to claim 12, further comprising attaching an antenna to a polarization unit, and tuning the locating device by pointing the antenna toward a reference entity and adjusting an axial ratio of the locating device by changing at least one of a length of the antenna and an exact relative position of the antenna compared to a position of other device components to obtain an optimum result based on a positional range from the locating device to the polarization unit.

16. A method of diagnosing a physiological condition of a human having a heart and conductive nerves, comprising the steps of:

detecting a polarization charge pattern by a manifested dielectrophoresis force to detect a change in local dielectrokinesis effects caused by an abnormal operation of the human's heart and conductive nerves.

* * * * *